United States Patent
Zhong et al.

(10) Patent No.: US 10,485,230 B2
(45) Date of Patent: Nov. 26, 2019

(54) SOLID ADJUVANT DEFOAMER

(71) Applicant: Dow Global Technologies LLC, Midland, MI (US)

(72) Inventors: Ling Zhong, Shanghai (CN); Jing Ji, Shanghai (CN); Jianhai Mu, Shanghai (CN)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/148,637

(22) Filed: Oct. 1, 2018

(65) Prior Publication Data

US 2019/0029249 A1 Jan. 31, 2019

Related U.S. Application Data

(63) Continuation of application No. 15/529,545, filed as application No. PCT/CN2014/092769 on Dec. 2, 2014, now Pat. No. 10,130,092.

(51) Int. Cl.
| | | |
|---|---|---|
| *A01N 25/14* | (2006.01) | |
| *B01D 19/04* | (2006.01) | |
| *A01N 25/30* | (2006.01) | |
| *A01N 43/653* | (2006.01) | |

(52) U.S. Cl.
CPC .......... *A01N 25/14* (2013.01); *A01N 25/30* (2013.01); *A01N 43/653* (2013.01); *B01D 19/0404* (2013.01)

(58) Field of Classification Search
None
See application file for complete search history.

(56) References Cited

U.S. PATENT DOCUMENTS

| | | | |
|---|---|---|---|
| 4,836,951 A | 6/1989 | Totten et al. | |
| 5,275,628 A | 1/1994 | Dimas et al. | |
| 5,460,698 A | 10/1995 | Nguyen | |
| 5,538,668 A | 7/1996 | Hendriks | |
| 6,413,908 B1 | 7/2002 | Reekmans et al. | |
| 7,550,514 B2 | 6/2009 | Rautschek et al. | |
| 2004/0091592 A1* | 5/2004 | Browne | B01D 19/0404 426/329 |
| 2006/0276554 A1 | 12/2006 | Dyllick-Brenzinger et al. | |
| 2008/0045415 A1 | 2/2008 | Baur et al. | |
| 2008/0214683 A1 | 9/2008 | Steinbrenner et al. | |
| 2009/0286684 A1 | 11/2009 | Scherl et al. | |
| 2015/0237852 A1 | 8/2015 | Zhong et al. | |

FOREIGN PATENT DOCUMENTS

| | | |
|---|---|---|
| CA | 920017 | 1/1973 |
| EP | 0831145 | 3/1998 |
| JP | A-S47-16284 | 5/1972 |
| JP | A-S52-2872 | 1/1977 |
| JP | 2000300907 | 10/2000 |
| JP | 2005279564 | 10/2005 |
| WO | 2004078312 | 9/2004 |

OTHER PUBLICATIONS

International Search Report and Written Opinion for related PCT Application PCT/CN2014/092769, dated Sep. 11, 2015 (10 pgs).

* cited by examiner

*Primary Examiner* — Robert A Wax
*Assistant Examiner* — Caralynne E Helm
(74) *Attorney, Agent, or Firm* — Brooks, Cameron & Huebsch, PLLC

(57) ABSTRACT

A defoaming adjuvant comprises a solid particulate carrier and a polyalkylene glycol adsorbed on to the solid particulate carrier, where the polyalkylene glycol is a reaction product of an alkyl alcohol initiator with 1,2-butylene oxide and, optionally, propylene oxide.

9 Claims, No Drawings

ID/T refers to Guobiao tuijian Chinese
SOLID ADJUVANT DEFOAMER

This application is a Continuation Application of U.S. National Stage Application Ser. No. 15/529,545, filed May 25, 2017 and published as U.S. Publication No. 2017/0325447 A1 on Nov. 16, 2017, which is a U.S. § 371 of International Application Number PCT/CN2014/092769, filed Dec. 2, 2014 and published as WO 2016/086349 on Jun. 9, 2016, the entire contents of which are incorporated herein by reference in its entirety.

BACKGROUND OF THE INVENTION

Field of the Invention

The present invention relates to a defoamer adjuvant that has a polyalkylene glycol containing butylene oxide adsorbed onto a solid carrier particle.

Introduction

Concentrates are a convenient and economical way to sell active components for formulations such as agrochemicals. Concentrates can be shipped with a minimal amount of carrier fluid, such as water, and then diluted in a carrier just prior to use by a consumer. That allows the manufacturer to avoid shipping water. However, consumers end up having to mix up their own formulations by mixing concentrate and carrier to achieve a usable formulation. That process can often result in foam formation during the mixing process, which can undesirably cause delays in preparing formulation and even loss of active if the foam froths out of the intended container. As a result, it is common for manufacturers to include defoamers in concentrate formulations to inhibit foam formation during dilution with a carrier.

Common defoamers for use in concentrates include organosilicone agents, perfluoroalkyl defoaming agents, and acetylenic diols. Organosilicone agents tend to be expensive and can decompose under conditions used to prepare solid formulations, thereby losing efficacy as a defoamer. Moreover, organosilicone agents tend to create cloudy solutions, which make them undesirable for clear formulations. Perfluoroalkyl defoaming agents and acetylenic diols are effective defoamers in liquid formulations, but are less effective as a solid adjuvant and can bind up so tightly as to lose their defoaming efficacy. Propylene oxide (PO) or PO and ethylene oxide (EO) copolymers have also had some reported success as defoamers.

It is desirable to identify a defoamer that is less costly than organosilicone defoamers, that is particularly effective as a solid adjuvant unlike perfluoroalkyl defoaming agents and acetylenic diols and that is more effective as a defoamer than PO and EO/PO copolymers.

BRIEF SUMMARY OF THE INVENTION

The present invention provides a defoamer that is less costly than organosilicone defoamers, that is particularly effective as a solid adjuvant unlike perfluoroalkyl defoaming agents and acetylenic diols and that is more effective as a defoamer than PO and EO/PO copolymers.

The present invention is a result of unexpectedly discovering that 1,2-butylene oxide (BO) containing polyalkylene glycol polymers become especially effective defoamers when adsorbed onto a solid substrate in the form of a solid adjuvant, even more effective than when they are introduced into a formulation in the liquid phase.

In a first aspect, the present invention is a defoaming adjuvant comprising: (a) a solid particulate carrier; and (b) a polyalkylene glycol adsorbed onto the solid particulate carrier, where the polyalkylene glycol is a reaction product of an alkyl alcohol initiator with 1,2-butylene oxide and, optionally, propylene oxide.

In a second aspect, the present invention is a method for using the defoaming adjuvant of the first aspect, the method comprising the step of formulating the defoaming adjuvant with an agrochemical to form an agrochemical formulation.

The present invention is useful as a defoamer adjuvant in compositions such as agrochemical concentrates.

DETAILED DESCRIPTION OF THE INVENTION

"And/or" means "and, or alternatively". All ranges include endpoints unless otherwise stated.

Test methods refer to the most recent test method as of the priority date of this document unless a date is indicated with the test method number as a hyphenated two digit number. References to test methods contain both a reference to the testing society and the test method number. Test method organizations are referenced by one of the following abbreviations: ASTM refers to ASTM International (formerly known as American Society for Testing and Materials); EN refers to European Norm; DIN refers to Deutsches Institut für Normung; and ISO refers to International Organization for Standards. GB/T refers to Guobiao tuijian Chinese national standard test methods issued by the Chinese National Committee of the International Organization for Standardization and International Electrotechnical Commission.

EO, PO and BO refer respectively to the copolymerized component of ethylene oxide, propylene oxide and 1,2-butylene oxide in a polyalkylene glycol polymer.

References to "CX" where "X" is a number refers to X number of carbons in a molecular component. For example, C12 means 12-carbons.

The solid particulate carrier of the present invention includes those commonly useful in agrochemical formulations. Suitable particulate carriers include any one or combination of more than one material selected from a group consisting of solid silica white, starch, diatomaceous earth, montmorillonite, calcium carbonate and bentonite. Desirably, the particulate carrier is solid silica selected from a group consisting of fumed, precipitated silica and silica made by a gel formation technique.

Desirably, the solid particulate carrier has an average particle size of 500 micrometers or smaller, preferably 400 micrometers or smaller, yet more preferably 300 micrometers or smaller, even more preferably 200 micrometers or smaller, still more preferably 100 micrometers or smaller and can be 10 micrometers or smaller, one micrometer or smaller and even 100 nanometers or smaller and at the same time the average particle size is desirably one nanometer or larger and typically 10 nanometers or larger and can be 100 nm or larger, one micrometer or larger, 10 micrometers or larger, 100 micrometers or larger and even 200 micrometers or larger. Determine average particle size by, for example, sieve analysis.

The polyalkylene glycol (PAG) of the present invention is adsorbed onto the solid particulate carrier. Desirably, PAG is present at an average concentration of one weight-percent (wt %) or more, preferably five wt % or more, more preferably 10 wt % or more, yet more preferably 15 wt % or more, even more preferably 20 wt % or more and can be present at a concentration of 25 wt % or more, 30 wt % or more, 35 wt % or more, 40 wt % or more, 45 wt % or more, 50 wt % or more, 55 wt % or more, 60 wt % or more and even 65 wt % or more. At the same time, PAG is typically present at a concentration of 80 wt % or less and is generally 75 wt % or less and can be 70 wt % or less, 65 wt % or less, 60 wt % or less, 55 wt % or less and even 50 wt % or less. It is most desirably for the concentration of PAG to be 50 wt % or more. Determine wt % PAG relative to combined weight of PAG and solid particulate carrier weight.

PAG can be adsorbed onto the particulate carrier by, for example, blending with the particulate material or spraying onto the particulate carrier.

The PAG is a reaction product of an alkyl alcohol initiator with 1,2-butylene oxide and, optionally, propylene oxide. The alcohol initiator can have one, two or three hydroxyl groups on it. That is, the alcohol initiator can be a monol, diol (for example, propylene glycol) or triol (for example, glycerol). The PAG can be capped or, preferably, is terminated with a hydroxyl end cap. Hence, the PAG can have the general formula:

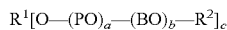

$$R^1[O-(PO)_a-(BO)_b-R^2]_c$$

where $R^1$ is the alkyl backbone remnant from the alkyl alcohol initiator, PO is a propylene oxide remnant after copolymerization, BO is a 1,2-butylene oxide remnant after polymerization, $R^2$ is either a hydrogen or another capping group such as an alkyl, —C(O)R or benzyl, and a and b designate the number PO and BO units in the PAG copolymer on average. The value for a can be zero while the value for b is greater than zero. The value for c is selected from one, two or three and corresponds to the number of hydroxyl groups on the alcohol initiator. The "end cap" for the PAG is the $R^2$ group combined with the oxygen of the alkoxy group to which it attaches. For example, when $R^2$ is a hydrogen the PAG is deemed to have a hydroxyl (—OH) end cap. When $R^2$ is an alkyl, the PAG has an ether (—$OR^2$) end cap and when $R^2$ is C(O)R the PAG has an ester (—OC(O)R) end cap.

The alkyl alcohol initiator corresponds to the structure $R^1[OH]_c$ where $R^1$ is the same in the alcohol structure and PAG structure above and c is the same value as c in the PAG structure above. The alkyl alcohol initiator, and therefore $R^1$, can contain one carbon or more and generally contains 30 carbons or less. Some desirable alkyl alcohol initiators (and $R^1$ groups) contains 6 or more, 8 or more carbons, 10 or more carbons, 12 or more carbons, 14 or more carbons 16 or more carbons, 18 or more carbons even 20 or more carbons on average over all PAG molecules. The PAG can comprise a combination of PAG molecules, each having $R^1$ carbon lengths within the scope of these suitable values. $R^1$ can be linear or branched where "linear" means that each carbon has only one or two carbons attached to it and "branched" means at least one carbon has at least three carbons attached to it. Examples of suitable alkyl alcohol initiators include those selected from dodecanol and 1,2-propylene glycol.

When both PO and BO are present, they may be present in blocks in any order (that is, either PO or BO can be attached to the $R^1O$ group) or randomly copolymerized in the PAG structure. The PAG can be free of PO and, hence, comprise only 1,2-butylene oxide. For avoidance of doubt, the PAG of the present invention is free of multiple copolymerized ethylene oxide units (that is, —$CH_2CH_2O$— units). When both PO and BO are present, it is desirable that PO be present at an average concentration of 20 wt % or more, preferably 30 wt % or more, more preferably 40 wt % or more, yet more preferably 50 wt % or more and PO can be present at a concentration of 60 wt % or more, 70 wt % or more and even 80 wt % or more while at the same time PO is desirably present at a concentration of 80 wt % or less, preferably 70 wt % or less, more preferably 60 wt % or less, yet more preferably 50 wt % or less and can be present at a concentration of 40 wt % or less, 30 wt % or less and even 20 wt % or less based on combined weight of PO and BO in the PAG.

The PAGs of the present invention desirably have an average molecular weight of 300 grams per mole (g/mol) or more, preferably 400 g/mol or more, and can have a molecular weight of 500 g/mol or more, 600 g/mole or more 700 g/mol or more, 800 g/mol or more, 900 g/mole or more and even 1000 g/mole or more while at the same time typically have a molecular weight of 3000 g/mol or less, preferably 2500 g/mole or less, more preferably 2000 g/mol or less and can have a molecular weight of 1500 g/mol or less, 1400 g/mol or less, 1300 g/mole or less, 1200 g/mol or less, 1100 g/mol or less, 1000 g/mol or less, 900 g/mol or less and even 800 g/mol or less. Molecular weights herein refer to weight average molecular weight unless otherwise stated. Determine PAG molecular weights from their hydroxyl number. Determine hydroxyl number and molecular weight according to ASTM D4274.

A surprising discovery with the present invention is the fact that there appears to be a synergistic defoaming effect between the solid particulate carrier and PAG component that accentuates the defoaming properties of the combined adjuvant over the defoaming property of either component individually. As demonstrated in the Examples section below, the adjuvant of the present invention comprising the PAG adsorbed onto a solid particulate carrier shows greater defoaming efficacy than either PAG alone or the solid particular carrier alone. This is unexpected and not universally true for all PAG materials. Therefore, there appears to be something special and unique about the BO-containing PAGs that facilitates this synergistic defoaming effect.

The defoaming adjuvant of the present invention can be free of conventional defoamers such as organosilocone materials, perfluoroalkyl materials and acetylenic diols. Also, the present invention can be free of surfactants enclosing the PAG on the surface of the solid particulate carrier. Some teachings specify that surfactants must enclose the defoamer on the surface of a particulate carrier, but that is not necessary in the present invention.

The defoaming adjuvant of the present invention is useful for use in the method of the present invention, which comprises formulating the defoaming adjuvant with an agrochemical such as a pesticide to form an agrochemical formulation. The formulation can be liquid or solid. The defoaming adjuvant and/or the formulation can be diluted with a solid or liquid carrier such as a solid filler and/or water to form a formulation. The benefit of the defoaming adjuvant is that when it is added to a liquid carrier the defoaming adjuvant serves to minimize foam formation.

EXAMPLES

Use the water dispersible granule formulation of tebuconazole listed in Table 1 to screen both the defoaming efficacy and dispersing performance for water dispersible formulations of these examples. Concentrations are in weight-percent relative to total formulation weight.

Prepare a water dispersible granule composition from the formulation in Table 1. First mix the components together and mechanically crush the mixture to reduce particle size. Add dropwise enough water to plasticize the mixture slightly (15-20 wt % based on total mixture weight). Add the plasticized composition to an extrusion granulating machine to form extruded granulated products and then dry at 50-60 degrees Celsius (° C.). The final product is obtained by sieving with 10, 20 and 40 mesh sieves.

TABLE 1

| Concentration (wt %) | Component | Component Description |
|---|---|---|
| 80 | Tebuconazole | Triazole fungicide. (RS)-1-(4-Chlorophenyl)-4,4-dimethyl-3-(1H,1,2,4-triazol-1-ylmethyl)pentane-3-ol |
| 5 | DURAMAX ™ D-518 dispersant | Acrylate polymer, polycarboxylate dispersing agent. DURAMAX is a trademark of Rohm and Haas Company. |
| 4 | OROTAN ™ SN dispersant | Naphthalene condensate. OROTAN is a trademark of Rohm and Haas Company. |
| 2 | AOS/92 | Alpha olefin sulfonate from Sinolight. CAS number 68439-57-6. |
| 9 | Calcium Carbonate | Filler. |

Antifoaming Efficacy Testing

To screen defoaming (actually, antifoaming) efficacy, the Persistent Foam Volume test method of GB/T 28137-2011, summarized as follows:

(1) Weigh approximately 180 grams (g) of standard water into a 250 milliliter (mL) graduated cylinder with glass stopper. The distance between the zero mark and the 250 mL mark of the cylinder is 20-21.5 centimeters (cm), and the distance between the 250 mL mark and the bottom of the stopper is 4-6 cm.
(2) Add 1.0 g of water dispersible granules into the water.
(3) Add standard water into the cylinder until the distance between the surface and the bottom of the stopper is 9 cm.
(4) Stopper the cylinder and invert 30 times within one minute.
(5) Place the cylinder upright and immediately record the foam height (initial ht) and record the foam height again after one minute (1 min ht).

standard water is 1000 mL of deionized water with 0.304 g anhydrous calcium chloride and 0.139 g magnesium chloride hexahydrate dissolved therein.

Dispersing Performance

Characterize the dispersibility of a water dispersible granule by adding a one gram sample of the water dispersible granule into 250 mL of water in a 250 mL graduated cylinder. Invert the graduated cylinder at a rate of two inversions per second. Record the number of inversions needed to completely dissolve the granules. Complete dissolution should occur within ten inversions.

Comparative Example (Comp Ex) A—Blank

Characterize the Antifoaming Efficacy and Dispersing Performance of the tebuconazole water dispersible granule formulation to establish a baseline performance without the presence of defoamer. In the antifoaming Efficacy Testing the initial ht is 63+/−6 mL and the 1 min ht is also 63+/−6 mL. In the Dispersing Performance test, complete dissolution occurs within 10 inversions.

Comp Exs B-F—Separate Defoamer Addition

Screen five different PAG defoamers, described in Table 2, for their efficacy in preventing foaming and breaking up foam that does form in during the Antifoaming Efficacy screening of the base tebuconazole formulation. Conduct the screening by completing steps (1)-(3) of the Antifoaming Efficacy test as in Comp Ex A but prior to step (4) add 0.01 g of one of the PAG defoamers from Table 2. Results from the Antifoaming Efficacy test are included in Table 2. Each formulation dispersed completely within 10 inversions in the Dispersing Performance evaluation.

The data in Table 2 reveals that each of the defoamers acts as an antifoaming agent in the formulation by reducing foam height from 63 mL as observed with the Blank to 40 mL or less.

TABLE 2

| Comp Ex | Defoamer | Description | Initial Ht (mL) | 1 Min Ht (mL) |
|---|---|---|---|---|
| B | DOWFAX ™ DF-106 defoamer | Polypropylene glycol, molecular weight of approximately 3800 g/mol. DOWFAX is a trademark of The Dow Chemical Company. | 35 | 35 |
| C | DOWFAX ™ DF142 | C12-C15 alcohol ethylene oxide/propylene oxide copolymer DOWFAX is a trademark of The Dow Chemical Company. | 30 | 30 |
| D | POLYGLYCOL P-4000E | Linear polypropylene glycol having a molecular weight of approximately 4000 g/mol. Available from The Dow Chemical Company. | 40 | 40 |
| E | UCON ™ OSP-18 | Dodecanol initiated random copolymer of propylene oxide and butylene oxide (50/50 by weight) with a typical kinematic viscosity of 4 centiStokes at 100° C., average molecular weight of 500 g/mol and a viscosity index of 123. UCON is a trademark of Union Carbide Corporation. | 35 | 35 |
| F | UCON ™ OSP-32 | Dodecanol initiated random copolymer of propylene oxide and butylene oxide (50/50 by weight) with a typical kinematic viscosity of 6.5 centiStokes at 100° C., average molecular weight of 760 g/mol and a viscosity index of 164. UCON is a trademark of Union Carbide Corporation. | 35 | 35 |

Comp Exs G-K—Neat Defoamer in Water Dispersible Granule

Prepare water dispersible granules using a modified form of the formulation in Table 1, modified by using 7 wt % calcium carbonate and 2 wt % of one of the defoamers listed in Table 2. The objective is to prepare water dispersible granules that have neat defoamer incorporated therein. Screen the resulting granules for Antifoaming Efficacy and Dispersing Performance.

Results for the different formulations are in Table 3. None of the granules completely disperse din the Dispersing Performance test.

TABLE 3

| Comp Ex | Defoamer | Initial Ht (mL) | 1 Min Ht (mL) |
|---|---|---|---|
| G | DOWFAX ™ DF-106 defoamer | 60 | 60 |
| H | DOWFAX ™ DF142 | 55 | 55 |
| I | POLYGLYCOL P-4000E | 60 | 60 |
| J | UCON ™ OSP-18 | 55 | 55 |
| K | UCON ™ OSP-32 | 60 | 60 |

The data in Table 3 reveals that each of the defoamers acts as an antifoaming agent to a much smaller extent when formulated as a need additive in the water dispersible granule, reducing foam height from 63 mL as observed with the Blank to 55-60 mL. The defoamers are all less effective formulated neat into the water dispersible granule than when added to a solution separate from the water dispersible granule.

Comp Exs L-R and Examples (Exs) 1-4—Solid Defoaming Adjuvant

Defoamers are once again formulated into the water dispersible granules but this time the defoamers are first formulated into a solid defoaming adjuvant by adsorbing the defoamer onto silica white particles. The silica white particles have an average particle size in a range of 100-200 micrometers, commercially available under the name NEWSIL™ C80 (NEWSIL is a trademark of Mc Ghan Nusil Corporation).

Prepare the solid defoaming adjuvant by placing 20 g of a defoamer into a 100 mL transparent bottle and begin slowly agitating. Slowly add silica white to the defoamer while agitating and avoiding clumping. Use a glass rod if necessary to break up any clumps that form. Add silica white powder to achieve a total composition that is approximately 35-40 wt % silica white and balance being defoamer. Table 4 discloses the composition of the solid defoaming adjuvants for use in this screening and the concentration of defoamer in the adjuvant as a wt % of total adjuvant weight. Notably, there are several additional defoamers used in this screening:

POLYGLYCOL P-1000E. Linear polypropylene glycol having a molecular weight of approximately 1000 g/mol. Available from The Dow Chemical Company.

POLYGLYCOL P-2000E. Linear polypropylene glycol having a molecular weight of approximately 2000 g/mol. Available from The Dow Chemical Company.

UCON™ OSP-320 synthetic polyalkylene glycol. A 1,2-propylene glycol initiated BO homopolymer, hydroxyl capped, with a typical kinematic viscosity at 40° C. of 320 centiStokes and average number average molecular weight of 2800 g/mol.

TANAFOAM SLX. Fatty acid, tallow, sodium salts available from Tanatex Chemicals.

TABLE 4

| Defoamer | Concentration of Defoamer on Solid Defoamer Adjuvant (wt %) |
|---|---|
| DOWFAX ™ DF106 | 65.1 |
| DOWFAX ™ DF142 | 64.6 |
| POLYGLYCOL P1000E | 64.1 |
| POLYGLYCOL P2000E | 64.8 |
| POLYGLYCOL P4000E | 64.6 |
| UCON ™ OSP-18 | 63.3 |
| UCON ™ OSP-32 | 65.7 |
| UCON ™ OSP-320 | 58.8 |

Screen the solid defoamer adjuvants in like manner as in Comp Exs G-K, except formulate the solid defoaming adjuvant instead of neat defoaming agent into the water dispersible granule. For consistency, formulate so as to obtain 1.5-1.7 wt % active defoamer in the water dispersible granule. Also screen an additional Comp Ex that screens just the silica white powder without a defoamer to reveal the effect of the silica white particles. Results are in Table 5. All water dispersible granules completely dissolved within 10 inversions in the Dispersing Performance screening. Defoamer concentration is in wt % relative to total water dispersible granule weight.

TABLE 5

| Example | Defoamer | Defoamer Concentration | Initial Ht | 1 Min Ht |
|---|---|---|---|---|
| Comp Ex L | (none) | 0 (1.58 wt % silica) | 63 | 63 |
| Comp Ex M | DOWFAX DF106 | 1.54 | 40 | 40 |
| Comp Ex N | DOWFAX DF142 | 1.55 | 50 | 45 |
| Comp Ex O | POLYGLYCOL P1000E | 1.56 | 65 | 65 |
| Comp Ex P | POLYGLYCOL P2000E | 1.54 | 50 | 45 |
| Comp Ex Q | POLYGLYCOL P4000E | 1.55 | 50 | 45 |
| Ex 1 | UCON ™ OSP-18 | 1.58 | 25 | 25 |
| Ex 2 | UCON ™ OSP-32 | 1.52 | 30 | 30 |
| Ex 3 | UCON ™ OSP-320 | 1.70 | 40 | 40 |
| Comp Ex R | Tanafoam SLX | 1.50 | 45 | 45 |

The data in Table 5 reveals a surprisingly synergistic affect at foam reduction when BO-containing PAG is adsorbed onto a solid particular carrier and then formulated into a water dispersible granule that is unique to the BO-containing PAGs. Comp Ex L reveals that silica powder (the solid particulate carrier) alone has no effect on the foam formation. Comp Exs M-Q also reveal that adsorbing PAGs without BO onto silica powder results in little increase in anti-foaming effect relative to the PAGs formulated into a water dispersible granule and decreased anti-foaming affect relative to PAG added separately from water dispersible granules.

In contrast, Exs 1-3 illustrate that the BO-containing PAGs show greater anti-foaming affect when adsorbed onto the particulate carrier and formulate into the water dispersible granule than when added separate from the water dispersible granule or formulated in any of the other ways into the water dispersible granule. This surprising unique behavior provides a beneficial increase in defoaming properties that is special for the BO-containing PAGs.

Comp Ex R provides a comparison to a standard defoaming additive for such formulations. The data reveals that the BO-containing PAGs also provide greater anti-foaming effect than the standard defoamer when the PAG is adsorbed onto a particulate carrier and formulated into the water dispersible granule.

The invention claimed is:
1. A defoaming adjuvant comprising:
   a. A solid particulate carrier; and
   b. A polyalkylene glycol adsorbed onto the solid particulate carrier, where the polyalkylene glycol is a reaction product of a 1,2-proplyene glycol initiator with 1,2-butylene oxide.

2. The defoaming adjuvant of claim 1, further characterized by the polyalkylene glycol having a hydroxyl end cap.

3. The defoaming adjuvant of claim 1, further characterized by the polyalkylene glycol having an average molecular weight in a range of 1000-3000 grams per mole.

4. The defoaming adjuvant of claim 1, further characterized by the solid particulate carrier being silica particles.

5. The defoaming adjuvant of claim 1, further characterized by being free of organosilocone materials, perfluoroalkyl materials and acetylenic diols.

6. The defoaming adjuvant of claim 1, wherein the defoaming adjuvant is free of surfactants enclosing the polyalkylene glycol on the surface of the solid particulate earner.

7. A method for using the defoaming adjuvant of claim 1, the method comprising the step of formulating the defoaming adjuvant with an agrochemical to form an agrochemical formulation.

8. The method of claim 7, further characterized by the agrochemicals comprising a pesticide.

9. The method of claim 7, further comprising the step of diluting the agrochemical formulation with water.

* * * * *